(12) United States Patent
Sugimoto

(10) Patent No.: US 9,984,896 B2
(45) Date of Patent: May 29, 2018

(54) HIGH-PURITY FLUORINATED HYDROCARBON, USE AS A PLASMA ETCHING GAS, AND PLASMA ETCHING METHOD

(71) Applicant: ZEON CORPORATION, Tokyo (JP)

(72) Inventor: Tatsuya Sugimoto, Tokyo (JP)

(73) Assignee: ZEON CORPORATION, Tokyo (JP)

(*) Notice: Subject to any disclaimer, the term of this patent is extended or adjusted under 35 U.S.C. 154(b) by 0 days. days.

(21) Appl. No.: 15/033,457

(22) PCT Filed: Oct. 28, 2014

(86) PCT No.: PCT/JP2014/078553
§ 371 (c)(1),
(2) Date: Apr. 29, 2016

(87) PCT Pub. No.: WO2015/064550
PCT Pub. Date: May 7, 2015

(65) Prior Publication Data
US 2016/0251286 A1 Sep. 1, 2016

(30) Foreign Application Priority Data
Oct. 30, 2013 (JP) ................................ 2013-225480

(51) Int. Cl.
| | |
|---|---|
| *H01L 21/3213* | (2006.01) |
| *C07C 17/00* | (2006.01) |
| *C09K 13/08* | (2006.01) |
| *C09K 13/00* | (2006.01) |
| *H01L 21/311* | (2006.01) |
| *H01L 21/3065* | (2006.01) |
| *H01L 21/3105* | (2006.01) |
| *C07C 19/08* | (2006.01) |
| *H01J 37/32* | (2006.01) |

(52) U.S. Cl.
CPC ........ *H01L 21/32137* (2013.01); *C07C 17/00* (2013.01); *C07C 19/08* (2013.01); *C09K 13/00* (2013.01); *C09K 13/08* (2013.01); *H01J 37/32009* (2013.01); *H01J 37/3244* (2013.01); *H01L 21/3065* (2013.01); *H01L 21/311* (2013.01); *H01L 21/3105* (2013.01); *H01L 21/31116* (2013.01); *H01L 21/32136* (2013.01); *H01J 2237/334* (2013.01)

(58) Field of Classification Search
None
See application file for complete search history.

(56) References Cited

U.S. PATENT DOCUMENTS 3,906,051 A 9/1975 Carter
2011/0068086 A1* 3/2011 Suzuki .............. H01L 21/31116
216/67

FOREIGN PATENT DOCUMENTS

| JP | 60-32718 A | 2/1985 |
| JP | 2009-292749 A | 12/2009 |
| WO | 2009/123038 A1 | 10/2009 |
| WO | 2014/104290 A1 | 7/2014 |

OTHER PUBLICATIONS

Written Opinion of the International Search Authority (English Translation) dated Jan. 27, 2015.*
P.N. Dastoor and E.U. Emovon, Journal of the Chemical Society, Faraday Transactions 1: Physical Chemistry in Condensed Phases; 1972, vol. 68, p. 2098-2102.*
International Search Report dated Jan. 27, 2015, issued in counterpart International Application No. PCT/JP2014/078553 (2 pages).
Takaoka et al.,"F-Propene-Dialkylamine Reaction Products as Fluorinating Agents", Bulletin of the Chemical Society of Japan, vol. 52, pp. 3377-3380, year 1979.
Olah et al., "Synthetic Methods and Reactions. 63.1 Pyridinium Poly(hydrogen fluoride) (30% Pyridine-70% Hydrogen Fluoride): A Convenient Reagent for Organic Fluorination Reactions", Journal of Organic Chemistry, vol. 44,1979, pp. 3872-3881.
Cooper et al., "Mechanism of Substitution at a Saturated Carbon Atom. Part VIII. Hydrolysis of tert.-Butyl Halides", Journal of Chemical Society, 1937, pp. 1183-1187.
Translation of Written Opinion dated Jan. 27, 2015, issued in counterpart International Patent Application No. PCT/JP2014/078553 (Form PCT/ISA237) (5 pages).
Extended European Search Report dated May 22, 2017, issued in European Patent Application No. 14858176.2.
Olah et al., "Syntheric Methods and Reaction. XIII. Preparation of Alkyl Halides from Alcohols with Alkali Halides in Polyhydrogen Fluoride/Pyridine Solution", Synthesis, No. 9, Jan. 1, 1974, pp. 653-654.

* cited by examiner

*Primary Examiner* — Jiong-Ping Lu
(74) *Attorney, Agent, or Firm* — Westerman, Hattori, Daniels & Adrian, LLP

(57) ABSTRACT

The present invention is a fluorohydrocarbon represented by R—F wherein R represents an isobutyl group or a t-butyl group), the fluorohydrocarbon having a purity of 99.9% by volume or more and a total butenes content of 1,000 ppm by volume or less; a use of the fluorohydrocarbon as a plasma etching gas; and a plasma etching method comprising selectively subjecting an inorganic nitride film stacked on silicon or a silicon oxide film to plasma etching using the fluorohydrocarbon.

4 Claims, No Drawings

HIGH-PURITY FLUORINATED HYDROCARBON, USE AS A PLASMA ETCHING GAS, AND PLASMA ETCHING METHOD

TECHNICAL FIELD

The present invention relates to a fluorohydrocarbon (isobutyl fluoride and t-butyl fluoride) that is useful as a plasma etching gas (e.g., etching gas and chemical vapor deposition (CVD) gas that are useful in the field of the production of a semiconductor device), a fluorine-containing medicine intermediate, and a hydrofluorocarbon-based solvent. In particular, the fluorohydrocarbon (isobutyl fluoride and t-butyl fluoride) that has been increased in purity is suitable as a plasma etching gas, a CVD gas, and the like in the field of the production of a semiconductor device that utilizes a plasma reaction.

BACKGROUND ART

Semiconductor production technology that achieves further miniaturization has been developed, and a line width of 20 nm or 10 nm has been used for a leading-edge process. The degree of difficulty in processing has increased along with an increase in the degree of miniaturization, and various techniques are currently under development using various approaches in terms of the materials, devices, processing methods, and the like.

In view of the above situation, the applicant of the present application developed a plasma etching gas that can deal with a leading-edge plasma etching process, and found that a saturated non-methane fluorohydrocarbon having a small number of fluorine atoms exhibits performance better than that of monofluoromethane that is widely used at present for etching a silicon nitride film (see Patent Literature 1).

However, semiconductor production technology that achieves further miniaturization has been developed in recent years, and higher performance has been desired for a plasma etching gas used for a plasma etching process.

It is known that isobutyl fluoride and t-butyl fluoride can be produced using several different methods.
(a) The following method is known as a method for producing isobutyl fluoride.
Patent Literature 2 discloses a method that reacts isobutyl alcohol with chlorotrimethylsilane in the presence of pyridine to obtain 1-trimethylsiloxy-2-methylpropane and brings 1-trimethylsiloxy-2-methylpropane into contact with diethylaminosulfur trifluoride (fluorinating agent) to obtain a mixture including isobutyl fluoride and t-butyl fluoride.
(b) With regard to a method for producing t-butyl fluoride,
Patent Literature 3 discloses that t-butyl fluoride was produced by bringing an n-pentane solution of t-butyl-lithium into contact with sulfur hexafluoride.
Non-Patent Literature 1 discloses that t-butyl fluoride was obtained in a yield of 78% by bringing t-butanol into contact with a diethylamine adduct of hexafluoropropene (fluorinating agent).
Non-Patent Literature 2 discloses that t-butyl fluoride was obtained in a yield of 60% by treating t-butanol with 60% hydrofluoric acid.
Non-Patent Literature 3 discloses that t-butyl fluoride was obtained in a yield of 60% by adding hydrogen fluoride to 2-methylpropene using a hydrogen fluoride-pyridine complex as a fluorinating agent.

CITATION LIST

Patent Literature

Patent Literature 1: WO2009/123038 (US2011/0068086A1)
Patent Literature 2: JP-A-60-32718
Patent Literature 3: JP-A-2009-292749

Non-patent Literature

Non-Patent Literature 1: Bulletin of the Chemical Society of Japan, Vol. 52, 3377 (1979)
Non-Patent Literature 2: Journal of Chemical Society, 1183 (1937)
Non-Patent Literature 3: Journal of Organic Chemistry, Vol. 44, 3872 (1979)

SUMMARY OF INVENTION

Technical Problem

An object of the invention is to provide high-purity fluorohydrocarbon (isobutyl fluoride and t-butyl fluoride), use of the high-purity fluorohydrocarbon as a plasma etching gas, and a plasma etching method.

Solution to Problem

The inventor of the invention used isobutyl fluoride and t-butyl fluoride obtained using the above methods as a gas for selectively subjecting a silicon nitride film stacked on silicon or a silicon oxide film to plasma etching. However, a large amount of hydrocarbon-based deposits were produced, and etching stopped when these gases were used.

The inventor conducted further extensive studies, and found that the above problem occurs when the butenes content in isobutyl fluoride or t-butyl fluoride is equal to or higher than a specific value. This finding has led to the completion of the invention.

Several aspects of the invention provide the following fluorohydrocarbon (see (1) to (3)), use of the fluorohydrocarbon as a plasma etching gas (see (4)), and plasma etching method (see (5)).
(1) A fluorohydrocarbon represented by R-F (wherein R represents an isobutyl group or a t-butyl group), the fluorohydrocarbon having a purity of 99.9% by volume or more and a total butenes content of 1,000 ppm by volume or less.
(2) The fluorohydrocarbon according to (1), the fluorohydrocarbon having a nitrogen content of 100 ppm by volume or less and an oxygen content of 50 ppm by volume or less.
(3) The fluorohydrocarbon according to (1), the fluorohydrocarbon having a water content of 50 ppm by volume or less.
(4) Use of the fluorohydrocarbon according to any one of (1) to (3) as a plasma etching gas.
(5) A plasma etching method including selectively subjecting an inorganic nitride film stacked on silicon or a silicon oxide film to plasma etching using the fluorohydrocarbon according to any one of (1) to (3) as a plasma etching gas.

Advantageous Effects of Invention

The invention thus provides a fluorohydrocarbon isobutyl fluoride and t-butyl fluoride) that has been increased in purity, and is useful as a plasma etching gas (e.g., etching gas and chemical vapor deposition (CVD) gas that are useful in the field of the production of a semiconductor device), a fluorine-containing medicine intermediate, and a hydrofluorocarbon-based solvent.

In particular, the fluorohydrocarbon (isobutyl fluoride and t-butyl fluoride) according to the invention that has been increased in purity is suitable as a plasma etching gas, a CVD gas, and the like in the field of the production of a semiconductor device that utilizes a plasma reaction.

DESCRIPTION OF EMBODIMENTS

The embodiments of the invention are described in detail below.
1) High-purity Fluorohydrocarbon A fluorohydrocarbon according to one embodiment of the invention is represented by the formula (1): R—F (wherein R represents an isobutyl group or a t-butyl group), the fluorohydrocarbon having a purity of 99.9% by volume or more and a total butenes content of 1,000 ppm by volume or less (hereinafter may be referred to as "fluorohydrocarbon (1)"). Specifically, the fluorohydrocarbon (1) is isobutyl fluoride and t-butyl fluoride.

The purity of the fluorohydrocarbon (1) and the butenes content in the fluorohydrocarbon (1) refer to values calculated from the peak area determined by gas chromatography using a flame ionization detector (FID). The butenes may be identified by gas chromatography-mass spectrometry.

The nitrogen content and the oxygen content in the fluorohydrocarbon (1) refer to values determined by gas chromatography using a thermal conductivity detector (TCD).

The water content in the fluorohydrocarbon (1) refers to a value determined by FT-IR.

Note that the term "butenes" used herein in connection with the fluorohydrocarbon (1) is a generic name for 1-butene (boiling point: −6.3° C.), 2-butene ((E)-2-butene (boiling point: 3.73° C.) and (Z)-2-butene (boiling point: 0.88° C.)), and isobutene (boiling point: −6.9° C.). One or more types of butenes included in the fluorohydrocarbon (1) are considered to be impurities.

Isobutyl fluoride that is the fluorohydrocarbon (1) may be produced using a method that fluorinates isobutanol using a fluorinating agent, a method that treats isobutyl bromide or an isobutyl alkylsulfonate with an alkali metal fluoride (e.g., potassium fluoride or cesium fluoride), or the like.

t-Butyl fluoride may be produced using a method that treats t-butanol with an amine complex of hydrofluoric acid or hydrogen fluoride, or the like.

The crude fluorohydrocarbon (1) obtained by the above production method may be purified by distillation (rectification). The butenes content in the fluorohydrocarbon) can be reduced to 1,000 ppm by volume or less, and preferably 500 ppm by volume or less, by purifying the crude fluorohydrocarbon (1) by rectification or the like.

Organic impurities including the butenes are removed from the crude fluorohydrocarbon (1) through purification by distillation.

A rectifying column having a moderate number of theoretical plates is used when purifying the crude fluorohydrocarbon (1) by means of distillation to remove organic impurities. The number of theoretical plates is normally about 10 to about 50, and preferably about 20 to about 50.

Since the boiling point of the butenes (impurities) is 5° C. or less, the efficiency of separation from the target isobutyl fluoride (boiling point: 20 to 22° C.) or t-butyl fluoride (boiling point: 12 to 13° C.) may apparently deteriorate at a temperature (e.g., room temperature) equal to or higher than the boiling point of the butenes due to a vaporization phenomenon within a fraction extraction line of the rectifying column. Therefore, it is preferable to sufficiently cool the fraction extraction line and a first fraction storage container.

The rectification pressure (gauge pressure) is normally set to a value between normal pressure and 10 atmospheres, and preferably set to a value between normal pressure and about 5 atmospheres. The ratio of the reflux rate to the distillate rate (hereinafter may be referred to as "reflux ratio") is preferably set to 30:1 or more in order to efficiently separate the butenes (particularly isobutene) that easily gasifies. If the reflux ratio is too low, it may be difficult to efficiently separate the butenes, and sufficiently increase the purity of the fluorohydrocarbon (1). Moreover, the amount of first fraction may increase, and the total amount of isobutyl fluoride or t-butyl fluoride (collected as a product) may decrease. If the reflux ratio is too high, collection (per extraction) may take time, and the rectification time may increase. As a result, productivity may deteriorate.

A batch-wise purification method or a continuous purification method may be used. A batch-wise purification method is preferably used when the production volume is small. When the production volume is large, a continuous purification method that utilizes several rectifying columns is preferably used. An extractive distillation operation that utilizes an extraction solvent may be performed in combination with rectification.

When the reaction conversion ratio is low, and it is necessary to collect the raw material, for example, a stepwise distillation operation (that separates the raw material compound by the first distillation, and separates the butenes (impurities) by the second distillation, for example) may be performed. In this case, it is also preferable to set the reflux ratio to 30:1 or more.

The nitrogen content and the oxygen content in the fluorohydrocarbon (1) may be reduced by utilizing a method that removes the butenes by means of rectification using an inert gas that belongs to Group 18 in the periodic table, a method that subjects the fluorohydrocarbon (1) to simple distillation, and extracts a fraction, or the like.

When using the latter method, the nitrogen content and the oxygen content in the fluorohydrocarbon (1) that remains in the still can be reduced by subjecting the fluorohydrocarbon (1) to simple distillation, and extracting nitrogen and oxygen together with the fluorohydrocarbon (1).

The ratio of the fluorohydrocarbon (1) to be extracted is preferably 20 to 50 wt %, and more preferably 30 to 40 wt %, based on the fluorohydrocarbon (1) that has been put in the still. The extracted fluorohydrocarbon (1) may be stored, and added to the next batch (i.e., recycled).

The nitrogen content in the fluorohydrocarbon (1) is preferably 100 ppm by volume or less, and more preferably 80 ppm by volume or less. The oxygen content in the fluorohydrocarbon (1) is preferably 50 ppm by volume or less, and more preferably 30 ppm by volume or less.

Water included in the fluorohydrocarbon (1) may be removed using a normal method such as a method that brings the fluorohydrocarbon (1) into contact with an adsorbent.

A molecular sieve (synthetic zeolite), alumina, or the like may be used as the adsorbent. It is preferable to use a molecular sieve 3A when drying a monofluorohydrocarbon or a difluorohydrocarbon such as 2-fluorobutane or 2,2-difluorobutane (see Japanese Patent Application No. 2012-165797).

A molecular sieve 4A, a molecular sieve 5A, and the like have a large pore size, and can reduce the water content in the same manner as a molecular sieve 3A. However, since a molecular sieve 4A, a molecular sieve 5A, and the like release nitrogen and oxygen adsorbed in the pores upon contact, the nitrogen content (concentration) and the oxygen content (concentration) in the fluorohydrocarbon (1) may increase.

When an alkaline molecular sieve is used, the fluorohydrocarbon (1) may easily undergo as dehydrofluorination reaction. Therefore, it is necessary to carefully select the molecular sieve.

When using alumina, it is preferable to use activated alumina having low crystallinity that is produced by subjecting alumina hydrate to thermal dehydration.

It is preferable to activate the adsorbent (e.g., molecular sieve or alumina) by means of calcination or the like before bringing the fluorohydrocarbon (1) into contact with the adsorbent, since the adsorbent can adsorb a larger amount of water.

The water content in the fluorohydrocarbon (1) can be reduced to 50 ppm by volume or less by brining the fluorohydrocarbon (1) into contact with the adsorbent.

If the water content in the fluorohydrocarbon (1) is high, water may adhere to (remain on) the processing target surface of a substrate after etching, and delamination of a laminate film may occur when forming a copper wire or the like, or the embedded wire may be corroded. Therefore, it is preferable to reduce the water content as much as possible.

Therefore, the water content in the fluorohydrocarbon (1) is preferably 50 ppm by volume or less, and more preferably 20 ppm by volume or less.

The fluorohydrocarbon (1) according to one embodiment of the invention that has been increased in purity can be obtained by purifying the crude fluorohydrocarbon (1) included in the elude reaction product by means of rectification so as to have a purity of 99.9% by volume or more and a butenes content of 1,000 ppm by volume or less (see above).

The purity of the fluorohydrocarbon (1) can be further increased by performing either or both of the step that brings the fluorohydrocarbon (1) into contact with the adsorbent to remove water, and the step that subjects the fluorohydrocarbon (1) to simple distillation to reduce the nitrogen content (concentration) and the oxygen content (concentration) in the fluorohydrocarbon (1) to preferably 100 ppm by volume or less and 50 ppm by volume or less (more preferably 50 ppm by volume or less and 20 ppm by volume or less).

The fluorohydrocarbon (1) according to one embodiment of the invention that has been increased in purity is useful as a plasma etching gas (e.g., etching gas and chemical vapor deposition (CVD) gas that are useful in the field of the production of a semiconductor device), a fluorine-containing medicine intermediate, and a hydrofluorocarbon-based solvent.

In particular, the fluorohydrocarbon (1) according to one embodiment of the invention that has been increased in purity is suitable as a plasma etching gas, a CVD gas, and the like in the field of the production of a semiconductor device that utilizes a plasma reaction.

2) Plasma Etching Gas

Another embodiment at the invention relates to use of the fluorohydrocarbon (1) according to one embodiment of the invention as a plasma etching gas.

The fluorohydrocarbon (1) according to one embodiment of the invention has etching selectivity with respect to an inorganic nitride film relative to silicon or a silicon oxide film.

When using the fluorohydrocarbon (1) according to one embodiment of the invention as a plasma etching gas, at least one inert gas selected from the group consisting of helium, neon, argon, xenon, and krypton may be used in combination with the fluorohydrocarbon (1) in order to control the concentration of etching species generated in plasma, and control the ion energy.

The inert gas is preferably used so that the volume ratio of the total inert gas to the fluorohydrocarbon (1) (inert gas/fluorohydrocarbon (1)) is 2 to 200, and more preferably 5 to 150.

Either or both of $O_2$ and $O_3$ ($O_2$ and/or $O_3$) may also be added to reduce an etching stop phenomenon. In this case, the volume ratio of $O_2$ and $O_3$ in total to the fluorohydrocarbon (1) (($O_2$ and $O_3$ in total)/fluorohydrocarbon (1)) is preferably set to 0.1 to 50, and more preferably 0.5 to 30.

3) Plasma Etching Method

A plasma etching method according to one embodiment of the invention includes selectively subjecting an inorganic nitride film stacked on silicon or a silicon oxide film to plasma etching using the fluorohydrocarbon (1) according to one embodiment of the invention as a plasma etching gas.

The etching target of the plasma etching method according to one embodiment of the invention is an inorganic nitride film.

Examples of the inorganic nitride film include a silicon nitride film, a silicon oxyninide film, a titanium nitride film, and the like.

The inorganic nitride film is normally formed on a substrate. Examples of the substrate include a glass substrate, a monocrystalline silicon wafer, a gallium arsenide substrate, and the like. A silicon film, a silicon oxide film, or the like may be formed on the substrate.

The plasma etching method according to one embodiment of the invention subjects a specific area of an inorganic nitride film stacked on silicon or a silicon oxide film to plasma etching using a resist pattern formed on the inorganic nitride film as a mask. The resist pattern may be formed by applying a photosensitive resist composition to a silicon oxide film to form a film, and patterning the film by applying radiation having a wavelength of 195 nm or less through a mask pattern, for example.

When implementing the plasma etching method according to one embodiment of the invention, the inorganic nitride film (etching target) provided with the resist pattern is placed in a chamber (etching chamber) provided with a plasma generation device. After evacuating the chamber, the fluorohydrocarbon (1) is introduced into the chamber at a specific flow rate optionally together with oxygen gas and a gas that belongs to Group 18 so that a specific pressure is achieved.

The flow rate of each process gas is set to be proportional to the ratio of each process gas. For example, the flow rate of the fluorohydrocarbon (1) is set to 5 to 30 sccm, the flow rate of the oxygen gas is set to 10 to 50 sccm, and the flow rate of the gas that belongs to Group 18 is set to 100 to 500 sccm.

The pressure inside the chamber into which the process gas has been introduced is normally 0.0013 to 1,300 Pa, and preferably 0.13 to 5 Pa.

A high-frequency electric field is then applied to the fluorohydrocarbon (1) introduced into the chamber using the plasma generation device to produce a glow discharge to generate plasma.

Examples of the plasma generation device include a helicon wave-type plasma generation device, a high-frequency induction-type plasma generation device, a parallel plate-type plasma generation device, a magnetron-type plasma generation device, a microwave-type plasma generation device, and the like. It is preferable to use a parallel plate-type plasma generation device, a high-frequency induction-type plasma generation device, or a microwave-type plasma generation device since high-density plasma can be easily generated.

The plasma density is not particularly limited. It is preferable to effect etching at a plasma density as high as $10^{12}$ ions/cm$^3$ or more, and more preferably $10^{12}$ to $10^{13}$ ions/cm$^3$, in order to more advantageously achieve the advantageous effects of the invention.

The temperature of the substrate that is reached during etching is not particularly limited, but is preferably −50 to +300° C., more preferably −20 to ±200° C. and still more preferably −10 to +100° C. The temperature of the substrate may or may not be controlled by means of cooling or the like.

The etching time is normally set to 5 to 10 minutes. Since the process gas used in connection with one embodiment of the invention can achieve high-speed etching, the productivity can be improved by setting the etching time to 2 to 5 minutes.

The plasma etching method according to one embodiment of the invention can easily and efficiently form a contact hole that has a very small diameter and a high aspect ratio and does not show necking.

EXAMPLES

The invention is further described below by way of examples. Note that the scope of the invention is not limited to the following examples. Note that the unit "%" refers to "wt %" unless otherwise indicated.

The following analysis conditions were used in connection with the examples.
Gas chromatography analysis (GC analysis)
Device: HP-6890 manufactured by Agilent Technologies
Column: Inert Cap-1 manufactured by GL Sciences Inc. (length: 60 m, inner diameter 0.25 mm, thickness: 1.5 µm)
Column temperature: held at 40° C. for 10 minutes, heated to 240° C. at 20° C./min, and held at 240° C. for 10 minutes
Injection temperature: 200° C.
Carrier gas: nitrogen
Split ratio: 100/1
Detector: FID
Analysis of impurities (gas chromatography-mass spectrometry)
GC device: HP-6890 manufactured by Agilent Technologies
Colmun: Inert Cap-1 manufactured by GL Sciences Inc. (length: 60 m, inner diameter 0.25 mm thickness: 1.5 µm)
Column temperature: held at 40° C. for 10 minutes, heated to 240° C. at 20° C./min and held at 240° C. for 10 minutes
MS device: 5973 NETWORK manufactured by Agilent Technologies
Detector: EI (accelerating voltage: 70 eV)
$^1$H-NMR analysis and $^{19}$F-NMR analysis
Device: JNM-ECA-400 manufactured by JEOL Ltd. (400 MHz)
Nitrogen and oxygen (gas chromatography analysis)
GC device HP-7890 manufactured by Agilent Technologies
Column: HP-5 manufactured by Agilent Technologies (length: 30 m, inner diameter 0.32 mm, thickness: 0.25 µm)
Column temperature: held at 40° C. for 5 minutes, heated to 65° C. at 5° C./min, and held at 65° C. for 1 minute
Gas sampler: 50° C.
Carrier gas: helium
Detector: pulse discharge detector
Measurement of water content (FT-IR)
IG-1000 manufactured by Otsuka Electronics Co., Ltd.
Cell material: barium fluoride
Cell length: 10 m Production Example 1

Synthesis of Methanesulfonyloxyisobutane

A 2 L glass reactor equipped with a stirrer, a dropping funnel, and a Dimroth condenser was charged with isobutanol (74 g), methanesulfonyl chloride (130 g), and dry diisopropyl ether (500 mL). The mixture was subjected to a nitrogen atmosphere. The reactor was cooled with ice water, and triethylamine (121 g) was added dropwise to the mixture from the dropping funnel over about 2 hours. After the dropwise addition, the mixture was stirred at 0° C. for 30 minutes, and then stirred at about 25° C. for 6 hours.

500 mL of ice water was added to the reaction mixture to dissolve triethylamine hydrochloride produced and separate the reaction mixture into two layers. The upper organic layer was sequentially washed with 5% hydrochloric acid, saturated sodium bicarbonate water, and a saturated sodium chloride solution, and dried over magnesium sulfate. Diisopropyl ether was evaporated using a rotary evaporator, followed by pumping up using a vacuum pump to obtain 118 g of crude methanesulfonyloxyisobutane.

Production Example 2

Synthesis of Isobutyl Fluoride

A 1 L glass reactor equipped with a stirrer, a dropping funnel, a fraction receiver, and a Dimroth condenser was charged with 116 g of spray-dried potassium fluoride (manufactured by Aldrich) and 800 mL of diethylene glycol. The mixture was subjected to a nitrogen atmosphere. The reactor was immersed in an oil bath, and heated at 95° C. 152 g of crude methanesulfonyloxyisobutane obtained by repeating the reaction of Production Example 1 was added to the mixture from the dropping funnel over about 3.5 hours. After the addition, the mixture was stirred for 4 hours, and the resulting low-boiling-point product was collected into the fraction receiver immersed in a dry ice-ethanol bath. After lowering the temperature of the oil bath to 80° C., two glass traps immersed in a dry ice-ethanol bath were connected to the reactor in series. A pressure controller and a vacuum pump were connected to the outlet of the glass trap. The vacuum pump was operated, and the pressure inside the system was lowered stepwise to 50 to 45 kPa, 35 to 30 kPa, and 30 to 25 kPa using the pressure controller to collect a volatile component into the glass trap.

The contents of the fraction receiver and the two glass traps were combined (49 g in total), and analyzed by gas chromatography. It was found that the mixture included isobutene (11.85% by area), isobutyl fluoride (79.69% by area), diisopropyl ether (7.32% by area), and a high-boiling-point component (1.14% by area).

Production Example 3

Synthesis of t-butyl Fluoride

A 300 mL glass reactor equipped with a rotator, a dropping funnel, and a Dimroth condenser was charged with 29 g of dry t-butanol and 120 mL of 1,1,2-trichlorotrifluoroethane. The mixture was cooled with ice water. A refrigerant (0° C.) was circulated through the Dimroth condenser. 94 g of a hexafluoropropene-diethylamine complex (manufactured by Tokyo Chemical Industry Co., Ltd.) was added dropwise to the mixture from the dropping funnel over about 45 minutes while stirring the mixture. After the dropwise addition, the mixture was stirred for 2 hours while cooling the mixture with ice water. The reaction mixture was then analyzed by gas chromatography, and it was found that t-butanol (raw material) had disappeared.

The reaction mixture was poured into a separating funnel containing ice water to wash the organic layer. The organic layer was then washed with cooled saturated sodium bicarbonate water and ice water, and dried over magnesium sulfate. The organic layer was filtered, and analyzed by gas chromatography. It was found that the organic layer was a mixture including isobutene (1.44% by area), t-butyl fluoride (23.86% by area), 1,1,2-trichlorotrifluoroethane (34.13% by area), and N,N-diethyl-2,3,3,3-tetrafluoropropionamide (39.52% by area).

Example 1

Rectification of Isobutyl Fluoride

A still was charged with 423 g of crude isobutyl fluoride obtained by repeating Production Examples 1 and 2, and a distillation operation was performed using a KS rectifying column (manufactured by Toka Seiki Co., Ltd., column length: 60 cm, packing material: Heli Pack No. 1). A refrigerant (−20° C.) was circulated through the condenser, and total reflux was effected for about 1 hour. The still was heated at 45 to 70° C. while observing the temperature of the top of the column and the amount of crude isobutyl fluoride remaining in the still. A fraction was then extracted at a reflux ratio of 45:1. 247 g of isobutyl fluoride (99.941% by area (volume)) was thus obtained. 543 ppm by area (volume) of isobutene was included in the isobutyl fluoride as impurities.

Spectral Data of Isobutyl Fluoride
$^1$H-NMR (CDCl$_3$, TMS) δ (ppm): 1.03 (t, 3H×2), 1.97 (m, 1H), 4.41 (m, 2H), 4.45 (m, 2H)
$^{19}$F-NMR (CDCl$_3$, CFCl$_3$) δ (ppm): −220 (m, F)

Example 2

A 1.7 L SUS316 container (of which the inner surface had been electropolished) charged with 100 g of a molecular sieve 3A (manufactured by Union Showa K.K.) was charged with 240 g of isobutyl fluoride obtained in Example 1, and the mixture was allowed to stand at about 25° C. for 22 hours.

A short column, a condenser, and a receiver were provided over a 0.5 L SUS316 still to assemble a simple distillation apparatus, and cooling water (−10° C.) was circulated through the condenser. 227 g of isobutyl fluoride from which water had been removed was put in the still, and the still was heated to 40° C. The nitrogen content (concentration) and the oxygen content (concentration) in the isobutyl fluoride (determined by gas chromatography) were 534 ppm by volume and 130 ppm by volume, respectively. The simple distillation operation was stopped when about 30 wt % of the isobutyl fluoride had been extracted into the receiver, and the still was cooled to 25° C. A 0.5 L manganese steel cylinder (inner surface roughness: 1S) equipped with a diaphragm-type valve was charged with 148 g of the isobutyl fluoride contained in the still. The isobutyl fluoride had a purity of 99.947% by area (volume), an isobutene content of 414 ppm by area (volume), a nitrogen content of 67 ppm by volume, an oxygen content of 10 ppm by volume, and a water content of 12 ppm by volume.

Example 3

A still was charged with 387 g of crude isobutyl fluoride obtained by repeating the reactions of Production Examples 1 and 2, and a distillation operation was performed using a KS rectifying column (manufactured by Toka Seiki Co., Ltd., column length: 60 cm, packing material: Heli Pack No. 1). A refrigerant (−20° C.) was circulated through the condenser, and total reflux was effected for about 1 hour. The still was heated from 45° C. to 70° C. while observing the temperature of the top of the column and the amount of crude isobutyl fluoride remaining in the still. A fraction was then extracted at a reflux ratio of 30:1. 213 g of isobutyl fluoride (99.913% by area (volume)) was thus obtained. 834 ppm by area (volume) of isobutene was included in the isobutyl fluoride as impurities.

Example 4

A 0.5 L stainless steel container was charged with 210 g of isobutyl fluoride obtained in Example 3, and 20 g of alumina ("N612N" manufactured by JGC Catalysts and Chemicals Ltd.). and the mixture was allowed to stand at 25° C. for 20 hours. The stainless steel container was connected to a 0.5 L manganese steel cylinder through a stainless steel tube, and the cylinder was charged with isobutyl fluoride under reduced pressure through a metal filter having a pore size of 0.2 μm. The cylinder was cooled with ice water, and about 20 g of isobutyl fluoride was extracted under a pressure of 5 to 10 kPa while reducing the pressure using a vacuum pump through a pressure controller. The isobutyl fluoride was returned to about 25° C. and allowed to stand for a while. The isobutyl fluoride had a purity of 99.918% by area (volume), an isobutene content of 791 ppm by area (volume), a nitrogen content of 41 ppm by volume, an oxygen content of 13 ppm by volume, and a water content of 38 ppm by volume.

Example 5

A still was charged with 423 g of crude t-butyl fluoride obtained by repeating Production Example 3, and a distillation operation was performed using a KS rectifying column (manufactured by Toka Seiki Co., Ltd., column length: 60 cm, packing material: Heli Pack No. 1). A refrigerant (−20° C.) was circulated through the condenser, and total reflux was effected for about 1 hour. The still was heated at 45 to 60° C. while observing the temperature of the top of the column and the amount of crude t-butyl fluoride remaining in the still. A fraction was then extracted at a reflux ratio of 40:1. 247 g of t-butyl fluoride (99.931% by area (volume)) was thus obtained. 627 ppm by area (volume) of isobutene was included in the t-butyl fluoride as impurities.

Spectral Data of t-butyl Fluoride
$^1$H-NMR (CDCl$_3$, TMS) δ (ppm): 1.26 (d, 3H×3)
$^{19}$F-NMR (CDCl$_3$, CFCl$_3$) δ (ppm): −130 (m, F)

Example 6

A 0.5 L SUS316 container (of which the inner surface had been electropolished) charged with 25 g of a molecular sieve 3A (manufactured by Union Showa K.K.) was charged with 240 g of t-butyl fluoride obtained in Example 5, and the mixture was allowed to stand at about 25° C. for 20 hours.

A short column, a condenser, and a receiver were provided over a 0.5 L SUS316 still to assemble a simple distillation apparatus, and cooling water (−15° C.) was circulated through the condenser. 231 g of t-butyl fluoride from which water had been removed was put in the still, and the still was heated to 30° C. The nitrogen content (concentration) and the oxygen content (concentration) in the t-butyl fluoride (determined by gas chromatography) were 710 ppm by volume and 266 ppm by volume, respectively. The simple distillation operation was stopped when about 35 wt % of the t-butyl fluoride had been extracted into the receiver, and the still was cooled to 25° C. A 0.5 L manganese steel cylinder (inner surface roughness: 1S) equipped with a diaphragm-type valve was charged with 144 g of the t-butyl fluoride contained in the still. The t-butyl fluoride had an isobutene content of 596 ppm by area (volume), a nitrogen content of 72 ppm by volume, an oxygen content of 22 ppm by volume, and a water content of 16 ppm by volume.

Example 7

A still was charged with 389 g of crude t-butyl fluoride obtained by repeating the reaction of Production Example 3, and a distillation operation was performed using a KS rectifying column (manufactured by Toka Seiki Co., Ltd., column length: 60 cm, packing material: Heli Pack No. 1). A refrigerant (−20° C.) was circulated through the condenser, and total reflux was effected for about 1 hour. The still was heated from 45° C. to 60° C. while observing the temperature of the top of the column and the amount of crude t-butyl fluoride remaining in the still. A fraction was then extracted at a reflux ratio of 30:1. 198 g of t-butyl fluoride (99.906% by area (volume)) was thus obtained. 902 ppm by area (volume) of isobutene was included in the t-butyl fluoride as impurities.

Example 8

A 0.5 L stainless steel container was charged with 187 g of t-butyl fluoride obtained in Example 7, and 18 g of a molecular sieve ("ZEOLUM (registered trademark) A-3" manufactured by Tosoh Corporation), and the mixture was allowed to stand at about 25° C. for 18 hours. The stainless steel container was connected to a 0.5 L manganese steel cylinder through a stainless steel tube, and the cylinder was charged with t-butyl fluoride under reduced pressure through a metal filter having a pore size of 0.2 μm. The cylinder was cooled with ice water, and about 20 g of t-butyl fluoride was extracted under a pressure of 5 to 10 kPa while reducing the pressure using a vacuum pump through a pressure controller. The t-butyl fluoride was returned to 25° C. and allowed to stand for a while. The t-butyl fluoride had an isobutene content of 889 ppm by area (volume), a nitrogen content of 66 ppm by volume, an oxygen content of 14 ppm by volume, and a water content of 39 ppm by volume.

Reference Example 1

A still was charged with 406 g of crude isobutyl fluoride obtained by repeating the reactions of Production Examples 1 and 2, and a distillation operation was performed using a KS rectifying column (manufactured by Toka Seiki Co., Ltd., column length: 60 cm, packing material: Heli Pack No. 1). A refrigerant (−20° C.) was circulated through the condenser, and total reflux was effected for about 1 hour. The still was heated at 45 to 70° C. while observing the temperature of the top of the column and the amount of crude isobutyl fluoride remaining in the still. A fraction was then extracted at a reflux ratio of 10:1. 235 g of isobutyl fluoride (99.872% by area (volume)) was thus obtained. 1,189 ppm by area (volume) of isobutene was included in the isobutyl fluoride as impurities. A cylinder was charged with 218 g of the isobutyl fluoride in the same manner as in Example 4. The nitrogen content, the oxygen content, and the water content in the isobutyl fluoride were measured, and found to be 40 ppm by volume, 13 ppm by volume, and 25 ppm by volume, respectively.

Reference Example 2

A still was charged with 393 g of crude t-butyl fluoride obtained by repeating the reaction of Production Example 3, and a distillation operation was performed using a KS rectifying column (manufactured by Toka Seiki Co., Ltd., column length: 60 cm, packing material: Heli Pack No. 1). A refrigerant (−20° C.) was circulated through the condenser, and total reflux was effected for about 1 hour. The still was heated at 45 to 70° C. while observing the temperature of the top of the column and the amount of crude t-butyl fluoride remaining in the still. A fraction was then extracted at a reflux ratio of 10:1. 225 g of t-butyl fluoride (99.811% by area) was thus obtained. 1,690 ppm by area (volume) of isobutene was included in the t-butyl fluoride as impurities. A cylinder was charged with 203 g of the t-butyl fluoride in the same manner as in Example 6. The nitrogen content, the oxygen content, and the water content in the t-butyl fluoride were measured, and found to be 55 ppm by volume, 11 ppm by volume, and 16 ppm by volume, respectively.

Example 9

Evaluation of plasma etching: A wafer on which a silicon nitride film was formed, and a wafer on which a silicon oxide film was formed, were etched separately. The etching rate of the silicon nitride film and the etching rate of the silicon oxide film were measured, and the selectivity ratio (SiN film/SiO$_2$ film) was calculated from the ratio of the etching rate of the silicon nitride film to the etching rate of the silicon oxide film.

Specifically, the wafer on which a silicon nitride film was formed, or the wafer on which a silicon oxide film was formed, was placed in an etching chamber of a parallel plate-type plasma etching apparatus. After evacuating the system, the silicon nitride film or the silicon oxide film was etched under the following etching conditions using the isobutyl fluoride obtained in Example 2. The etching rate of the silicon nitride film was 28 nm/min, and the silicon oxide film was not etched. Specifically, the selectivity ratio (SiN film/SiO$_2$ film) was infinity Etching Conditions
Mixed gas pressure: 6.7 Pa
Power supplied to upper electrode from high-frequency power supply: 200 W
Power supplied to lower electrode from high-frequency power supply: 100 W
Interval between upper electrode and lower electrode: 50 mm
Electrode temperature: 20° C.
Gas Flow Rate
$O_2$ gas: 60 sccm
Isobutyl fluoride: 45 sccm
Etching time 180 sec Example 10

An etching evaluation process was performed in the same manner as in Example 9, except that the isobutyl fluoride obtained in Example 4 was used. The etching rate of the silicon nitride film was 2 nm/min, and the silicon oxide film was not etched. Specifically, the selectivity ratio (SiN film/$SiO_2$ film) was infinity.

Example 11

An etching evaluation process was performed in the same manner as in Example 9 under the following conditions, except that the t-butyl fluoride obtained in Example 6 was used instead of the isobutyl fluoride. The etching rate of the silicon nitride film was 30 nm/min, and the silicon oxide film was not etched. Specifically, the selectivity ratio (SiN film/$SiO_2$ film) was infinity.
Etching Conditions
Mixed gas pressure: 6.7 Pa
Power supplied to upper electrode from high-frequency power supply: 200 W
Power supplied to lower electrode from high-frequency power supply: 100 W
Interval between upper electrode and lower electrode: 50 mm
Electrode temperature: 20° C.
Gas Flow Rate
$O_2$ gas: 60 sccm
t-Butyl fluoride: 40 sccm
Etching time: 180 sec Example 12

An etching evaluation process was performed in the same manner as in Example 11, except that the t-butyl fluoride obtained in Example 8 was used. The etching rate of the silicon nitride film was 24 nm/min, and the silicon oxide film was not etched. Specifically, the selectivity ratio (SiN film/$SiO_2$ film) was infinity.

Comparative Example 1

An etching evaluation process was performed in the same manner as in Example 9, except that the isobutyl fluoride obtained in Reference Example 1 was used. However, etching stopped halfway due to the occurrence of deposition on the silicon nitride film. The silicon oxide film was not etched.

Comparative Example 2

An etching evaluation process was performed in the same manner as in Example 11, except that the t-butyl fluoride obtained in Reference Example 2 was used. However, etching stopped halfway due to the occurrence of deposition on the silicon nitride film. The silicon oxide film was not etched.

The invention claimed is:

1. A plasma etching method comprising selectively subjecting an inorganic nitride film stacked on silicon or a silicon oxide film to plasma etching using a fluorohydrocarbon represented by R—F (wherein R represents an isobutyl group), the fluorohydrocarbon having a purity of 99.9% by volume or more, the fluorohydrocarbon comprising: a total butenes content from 414 ppm to 1,000 ppm by volume; a nitrogen content of 100 ppm by volume or less; and an oxygen content of 50 ppm by volume or less as a plasma etching gas,
    wherein the fluorohydrocarbon has been prepared by fluorinating isobutanol by using a fluorinating agent or by treating isobutyl bromide or an isobutyl alkylsulfonate with an alkali metal fluoride, followed by distillation.

2. The plasma etching method according to claim 1, wherein a selectivity ratio of the nitride film over the silicon oxide film is infinity.

3. A plasma etching method comprising selectively subjecting an inorganic nitride film stacked on silicon or a silicon oxide film to plasma etching using a fluorohydrocarbon represented by R—F (wherein R represents a t-butyl group), the fluorohydrocarbon having a purity of 99.9% by volume or more, the fluorohydrocarbon comprising: a total butenes content from 414 ppm to 1,000 ppm by volume; a nitrogen content of 100 ppm by volume or less; and an oxygen content of 50 ppm by volume or less as a plasma etching gas,
    wherein the fluorohydrocarbon has been prepared by treating t-butanol with an amine complex of a hydrofluoric acid or a hydrogen fluoride, followed by distillation.

4. The plasma etching method according to claim 3, wherein a selectivity ratio of the nitride film over the silicon oxide film is infinity.

* * * * *